US00PP16946P3

(12) United States Plant Patent

Iredell et al.

(10) Patent No.: US PP16,946 P3

(45) Date of Patent: Aug. 8, 2006

(54) *BOUGAINVILLEA* PLANT NAMED 'BEESNEES'

(50) Latin Name: *Bougainvillea hybrida*
Varietal Denomination: Beesnees

(75) Inventors: Peter Iredell, Moggil Brisbane (AU); Jan Iredell, Moggil Brisbane (AU)

(73) Assignee: Bougainvillea Nursery, Queensland (AU)

( * ) Notice: Subject to any disclaimer, the term of this patent is extended or adjusted under 35 U.S.C. 154(b) by 0 days.

(21) Appl. No.: 10/973,066

(22) Filed: Oct. 23, 2004

(65) Prior Publication Data

US 2005/0262611 P1 Nov. 24, 2005

(51) Int. Cl.
*A01H 5/00* (2006.01)

(52) U.S. Cl. ..... Plt./256

(58) Field of Classification Search ..... Plt./256
See application file for complete search history.

(56) References Cited

PUBLICATIONS

Plant Varieties Journal, Quarter Two 2002, vol. 15, No. 2, p. 25 and 103.*

UPOV–ROM, GTI Jouve Retrieval Software, Plant Variety Database, 2005/01, hit on 'Beesnees'.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Bougainvillea* plant named 'Beesnees', characterized by its outwardly spreading and bushy plant habit; vigorous growth habit; dark green-colored fully expanded leaves; freely flowering habit; and pure white-colored flower bracts.

1 Drawing Sheet

Botanical classification/cultivar designation: *Bougainvillea hybrida* cultivar Beesnees.

BACKGROUND OF THE INVENTION

The present Invention relates to a new and distinct cultivar of *Bougainvillea* plant, botanically known as *Bougainvillea hybrida,* and hereinafter referred to by the name 'Beesnees'.

The new *Bougainvillea* is a naturally-occurring branch mutation of the *Bougainvillea hybrida* cultivar Panda, not patented. The new *Bougainvillea* was discovered and selected by the Inventors from within a population of plants of the cultivar Panda in a controlled environment in Moggill, Queensland, Australia in 1996. The selection of this plant was based on its attractive flower coloration and non-variegated leaves.

Asexual reproduction of the new cultivar by cuttings at Moggill, Queensland, Australia since 1997, has shown that the unique features of this new *Bougainvillea* are stable and reproduced true to type in successive generations.

SUMMARY OF THE INVENTION

Plants of the cultivar Beesnees have not been observed under all possible environmental conditions. The phenotype may vary somewhat with variations in environment such as temperature and/or light intensity without, however, any variance in genotype.

The following traits have been repeatedly observed and are determined to be the unique characteristics of 'Beesnees'. These characteristics in combination distinguish 'Beesnees' as a new and distinct cultivar:

1. Outwardly spreading and bushy plant habit.

2. Vigorous growth habit.
3. Dark green-colored fully expanded leaves.
4. Freely flowering habit.
5. Pure white-colored flower bracts.

Plants of the new *Bougainvillea* are most similar to plants of the parent, the cultivar Panda. In side-by-side comparisons conducted in Moggill, Queensland, Australia, plants of the new *Bougainvillea* differed from plants of the cultivar Panda in the following characteristics:

1. Plants of the new *Bougainvillea* rooted more quickly than plants of the cultivar Panda.
2. Plants of the new *Bougainvillea* grew faster than plants of the cultivar Panda.
3. Plants of the new *Bougainvillea* had solid green-colored leaves whereas plants of the cultivar Panda had variegated leaves.
4. Plants of the new *Bougainvillea* were more freely flowering than plants of the cultivar Panda.
5. Plants of the new *Bougainvillea* and the cultivar Panda differed in flower bract coloration as flower bracts of plants of the cultivar Panda were slightly discolored.

Plants of the new *Bougainvillea* can also be compared to plants of the cultivar Nonya, not patented. In side-by-side comparisons conducted in Moggill, Queensland, Australia, plants of the new *Bougainvillea* differed primarily from plants of the cultivar Nonya in flower bract coloration as flower bracts of plants of the cultivar Nonya were mauve-colored.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ from the color values cited in the detailed botanical description which accurately describe the colors of the new *Bougainvillea*.

The photograph at the top of the sheet is a side perspective view of typical one-year old plants of 'Beesnees' grown in the landscape.

The photograph in the middle of the sheet is a close-up view of typical developing flowers of 'Beesnees'.

The photograph at the bottom of the sheet is a close-up view of typical developing leaves of 'Beesnees'.

DETAILED BOTANICAL DESCRIPTION

In the following description, color references are made to The Royal Horticultural Society Colour Chart, 2001 Edition, except where general terms of ordinary dictionary significance are used. Plants used for the following botanical description were grown in Moggill, Queensland, Australia in a polyethylene-covered greenhouse. Plants used for the description were about one to two years old.

Botanical classification: *Bougainvillea hybrida* cultivar Beesnees.

Parentage: Naturally-occurring branch mutation of the *Bougainvillea hybrida* cultivar Panda, not patented.

Propagation:

*Type.*—By cuttings.

*Time to initiate roots.*—About one week at 25° C.

*Time to develop roots.*—About two weeks at 25° C.

*Root description.*—Thick; white in color.

Plant description:

*Form.*—Outwardly spreading and bushy plant habit; vigorous growth habit. Freely branching with lateral branches potentially developing at every node.

*Plant height, soil level to top of plant plane.*—About 1 to 1.5 meters.

*Plant width.*—About 1 to 1.5 meters.

*Stem color.*—1B.

*Stem texture.*—Smooth, glabrous.

*Thorns.*—Length: About 8 mm to 15 mm. Diameter: About 1.75 mm to 2 mm. Color: 199B.

*Foliage description.*—Arrangement: Opposite, simple. Length: About 7.4 cm. Width: About 4.1 mm. Shape: Elliptic. Apex: Acuminate. Base: Cuneate. Margin: Entire; slightly undulate. Texture, upper and lower surfaces: Smooth, glabrous. Venation pattern: Pinnate. Color: Developing foliage, upper surface: 144A; towards the center, 144C; "watermark variegation". Developing foliage, lower surface: 144A; towards the center, 144B. Fully expanded foliage, upper surface: 139A; towards the center, 146A; watermark variegation not apparent. Fully expanded foliage, lower surface: 144A; towards the center, 144B. Venation, upper surface: 144A. Venation, lower surface: 152C. Petiole length: About 1.5 cm. Petiole diameter: About 1 mm. Petiole texture, upper and lower surfaces: Smooth, glabrous. Petiole color, upper surface: 139A. Petiole color, lower surface: 152C.

Flower description:

*Flower type and habit.*—Single flowers arranged in axillary panicles with showy bracts. Flowers face mostly upright. Flowers not persistent.

*Fragrance.*—None.

*Natural flowering season.*—Cyclically flowering year-round in Moggill, Queensland, Australia; flowering periods about six to twelve weeks long.

*Quantity.*—Freely flowering with about 25 flowers per panicle.

*Flower longevity.*—About six to ten days.

*Flower diameter.*—About 6 mm.

*Flower depth (height).*—About 1.8 cm.

*Flower buds.*—Length: About 1.2 cm. Diameter: About 2.5 mm. Shape: Elongated. Color: 1D.

*Petals.*—Quantity per flower: About five; fused tubular corolla. Length: About 2 cm. Width: About 3.5 mm. Shape: Fan-shaped. Apex: Emarginate. Margin: Entire. Texture, upper and lower surfaces: Smooth; glabrous. Color: When opening, upper and lower surfaces: 158C. Fully opened, upper surface: 160D. Fully opened, lower surface: 158B.

*Sepals.*—Quantity per flower: About five; fused tubular corona. Length: About 2 cm. Diameter: About 4 mm. Shape: Linear. Apex: Acute. Margin: Entire. Color: When opening, upper and lower surfaces: N144C. Fully opened, upper and lower surfaces: N144C.

*Flower bracts.*—Quantity per flower: Three. Length: About 3.3 cm. Width: About 2.5 cm. Shape: Ovate. Apex: Acute. Base: Cordate. Margin: Entire; slightly undulate. Texture, upper and lower surfaces: Smooth; glabrous; rugose. Color: When opening, upper and lower surfaces: 155C. Fully opened, upper and lower surfaces: 155C.

*Peduncles.*—Length: About 1.1 cm. Diameter: About 1.5 mm. Texture: Smooth, glabrous. Angle: About 45° from vertical. Strength: Strong. Color: 151A.

*Pedicels.*—Length: About 9 mm. Diameter: About 1 mm. Texture: Smooth, glabrous. Angle: About 45° from vertical. Strength: Strong. Color: 151A.

*Reproductive organs.*—Androecium: Stamens per flower: About seven. Anther shape: Oblong. Anther length: About 0.75 mm. Anther color: 13C. Pollen color: 13C. Gynoecium: Quantity of pistils per flower: One. Pistil length: About 1.1 cm. Stigma shape: Linear. Stigma color: 4D. Style length: About 2 mm. Style color: 144D. Ovary color: 144B.

*Seeds/fruits.*—Seed and fruit development has not been observed.

Disease/pest resistance: Under commercial production conditions, plants of the new *Bougainvillea* have not been noted to be resistant to pathogens or pests common to *Bougainvillea*.

Garden performance: Plants of the new *Bougainvillea* have good garden performance as plants of the new *Bougainvillea* have been observed to tolerate wind, rain and temperatures from 3 to 40° C.

It is claimed:

1. A new and distinct cultivar of *Bougainvillea* plant named 'Beesnees', as illustrated and described.

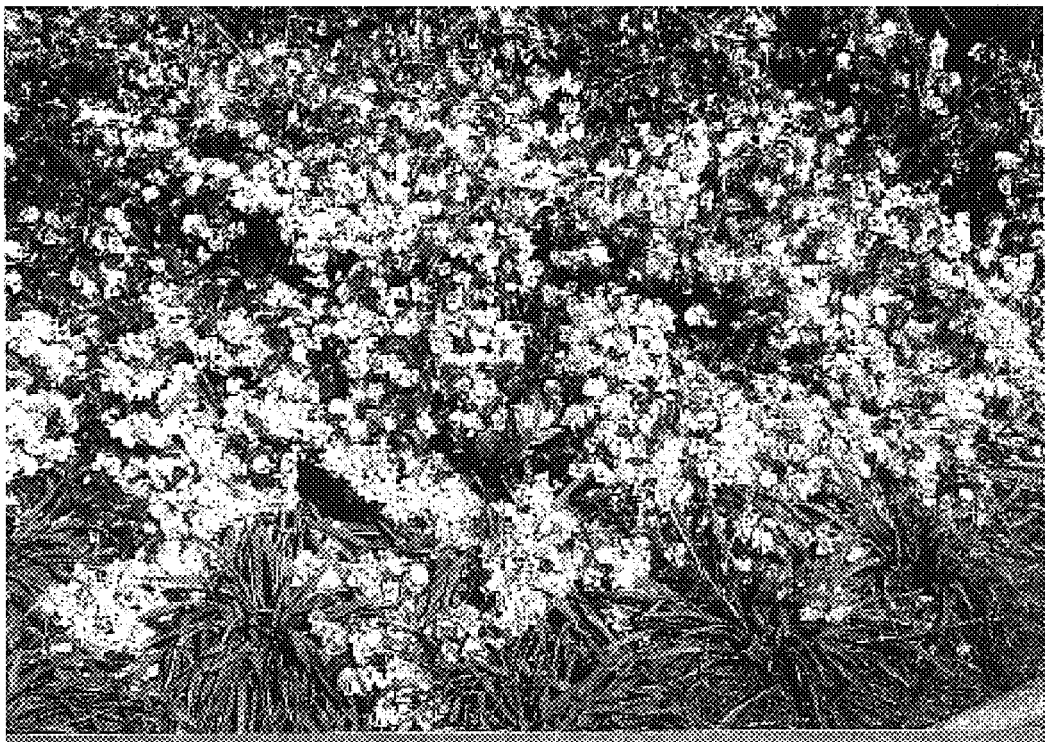
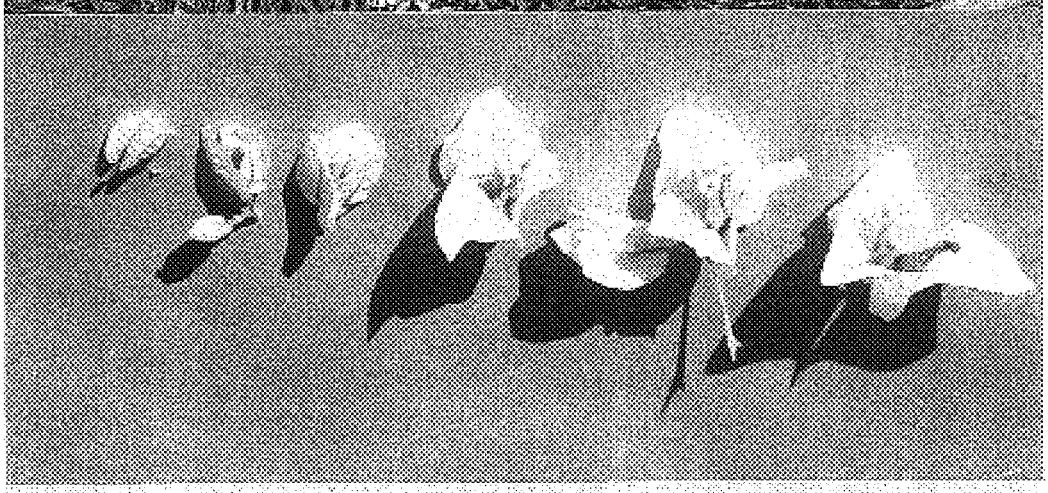
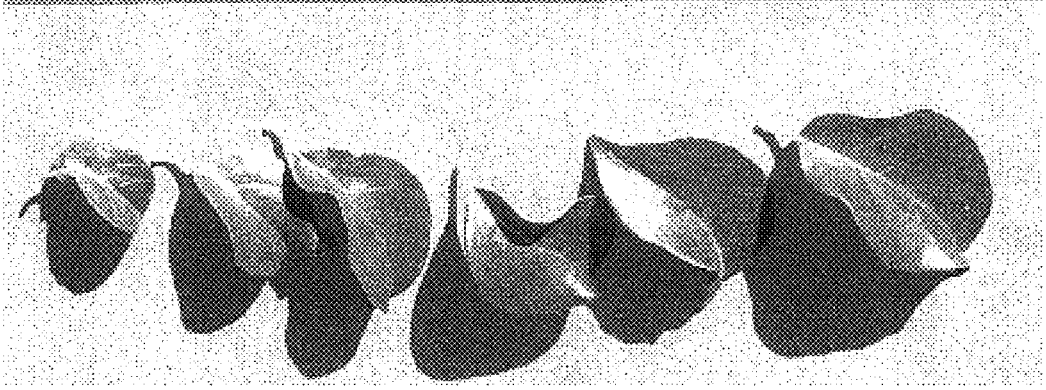

* * * * *